(12) United States Patent  
Venturino et al.

(10) Patent No.: US 7,848,490 B2
(45) Date of Patent: Dec. 7, 2010

(54) METHOD FOR ASSOCIATING A WIRELESS DETECTOR WITH AN IMAGING APPARATUS

(75) Inventors: Michael Venturino, Geneseo, NY (US); Peter A. Newman, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 38 days.

(21) Appl. No.: 12/269,090

(22) Filed: Nov. 12, 2008

(65) Prior Publication Data

US 2009/0130983 A1 May 21, 2009

Related U.S. Application Data

(60) Provisional application No. 60/989,155, filed on Nov. 20, 2007.

(51) Int. Cl.
*H05G 1/64* (2006.01)
(52) U.S. Cl. .................................. 378/98.8; 378/116
(58) Field of Classification Search ............... 378/62, 378/98.8, 207, 116, 117
See application file for complete search history.

(56) References Cited

U.S. PATENT DOCUMENTS

2007/0165783 A1* 7/2007 Abu Tabanjeh ............. 378/116

FOREIGN PATENT DOCUMENTS

| EP | 1 857 048 | 11/2007 |
| WO | WO2004/112446 | 12/2004 |
| WO | WO2006/095538 | 9/2006 |

* cited by examiner

*Primary Examiner*—Courtney Thomas (57) ABSTRACT

A method for obtaining an x-ray image stores an association between a digital radiology receiver panel, a label that is applied to one or more surfaces of the digital radiology receiver panel, and an x-ray imaging room. A response to an operator instruction designates the digital radiology receiver panel having the stored association as an active digital radiology receiver panel in the x-ray imaging room. Instructions are transmitted wirelessly to the active digital radiology receiver panel. Image data is obtained from the active digital radiology receiver panel following exposure to x-ray radiation.

17 Claims, 8 Drawing Sheets

METHOD FOR ASSOCIATING A WIRELESS DETECTOR WITH AN IMAGING APPARATUS

CROSS REFERENCE TO RELATED APPLICATIONS

Priority is claimed from U.S. Ser. No. 60/989,155, provisionally filed on Nov. 20, 2007, entitled "DETECTOR LABEL AND CONSOLE ICON CODING SCHEME FOR A WIRELESS DR DETECTOR SYSTEM", in the name of Michael Venturino, commonly assigned and incorporated herein by reference.

FIELD OF THE INVENTION

The invention relates generally to diagnostic imaging systems and more particularly to managing communication between an imaging system and a digital radiography receiver panel.

BACKGROUND OF THE INVENTION

Digital radiography (DR) is increasingly accepted as an alternative to film-based imaging technologies that rely on photosensitive film layers to capture radiation exposure and thus to produce and store an image of a subject's internal physical features. With digital radiography, the radiation exposure energy captured on radiation sensitive layers is converted, pixel by pixel, to electronic image data which is then stored in memory circuitry for subsequent read-out and display on suitable electronic image display devices. One of the driving forces in the success of digital radiography is the ability to rapidly visualize and communicate stored images via data networks to one or more remote locations for analysis and diagnosis by the radiologist, without the delay that results when film must be developed and checked, then packaged and mailed or sent by courier to a remote location or when the film must be input to a separate scanner apparatus to provide digitized image data.

DR systems enjoy some advantages over conventional film-based or computed radiography (CR) systems. An advantage is the capability of the DR system to obtain radiographic image data without the need for an operator or technologist to move, handle, process, or scan any type of imaging medium following exposure. Data downloaded directly from the DR receiver panel is then quickly available for viewing and diagnosis on-site or at any appropriately networked viewer workstation. Other advantages include the capability to work with existing hardware components that generate x-ray radiation, its reduced dependence on operator performance, and its low-profile receiver designs that are compatible with receiver dimensions used for film and CR systems.

Early DR receiver panels were integrated into the x-ray system, with the interconnect cables and wiring appropriately routed out of the way of the operator, allowing the DR panel to be suitably positioned relative to the patient. Recently, portable DR receiver panels are being introduced. These portable detectors are typically powered by on-board batteries and communicate wirelessly with control panel and computer storage and display components. This makes these DR receiver panels flexible to work with and enables them to be used in place of film or CR cassettes in retrofit configurations.

While portability and wireless operation offer advantages for DR receiver panels, however, these same features also introduce potential problems in identifying the specific DR receiver panel that is being used in a multi-panel environment, so that errors in device reset or addressing can occur. Unlike the conventional x-ray film cassette or CR cassette that is routinely removed after each exposure in order to further process the medium and obtain the image, the DR receiver panel can remain in place. Where there are multiple DR receiver panels accessible from a system, the operator must be able to positively identify the specific DR panel that is in place for obtaining each image. Otherwise, it would be possible to address, reset, and collect data from the wrong DR receiver panel. Without some method for minimizing the likelihood of this type of error, there is a higher risk of unnecessary additional patient exposure due to re-takes as well as inefficiency, confusion, and wasted time and effort.

SUMMARY OF THE INVENTION

It is an object of the present invention to address the need for a systematic method to minimize the risk of inadvertent over-exposure to the patient and to improve the management of DR receiver panel allocation at a facility that has multiple x-ray imaging rooms. With this object in mind, the present invention provides a method for obtaining an x-ray image comprising: storing an association between a digital radiology receiver panel, a label that is applied to one or more surfaces of the digital radiology receiver panel, and an x-ray imaging room; responding to an operator instruction by designating the digital radiology receiver panel having the stored association as an active digital radiology receiver panel in the x-ray imaging room; transmitting wireless instructions to the active digital radiology receiver panel; and obtaining image data from the active digital radiology receiver panel following exposure to x-ray radiation.

An advantage of the method is that it allows wireless DR radiography receiver panels to be transferred between different x-ray systems while maintaining a unique identity with respect to system and operator use. Storing and using the association of each DR receiver panel within a hospital or other facility can help to make use of resources more efficient as well as to reduce the likelihood of unnecessary patient exposure.

These objects and advantages are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

The following is a detailed description of the preferred embodiments of the invention, reference being made to the drawings in which the same reference numerals identify the same elements of structure in each of the several figures.

The apparatus and method of the present invention address the need for a systematic way to identify the appropriate DR receiver panel to receive an exposure in an environment in which there may be multiple portable DR receiver panels.

The present application uses the term "imaging room" or more simply "room" as it is conventionally used and understood by those practiced in the radiology arts, to apply to an installation of an x-ray imaging apparatus or system at a specific location that has one or more DR receiver panels that can be assigned to that system. There is generally an organizational hierarchy for x-ray rooms in a given facility. One or more imaging rooms may be grouped together as part of a "department" within a hospital or other facility in which x-rays are obtained. For example, the emergency room may be considered as a department and may itself have two or more rooms for x-ray imaging. There may then be a number of departments within a hospital or other care facility, which is generally termed a "site" or "facility" in the context of the present disclosure. The problems addressed by embodiments of the present invention are of particular relevance where a hospital or other type of site has multiple departments for DR radiological imaging and more particularly where each department can have multiple rooms.

The terms "set" and "subset" have their conventional meaning as groupings of elements and, unless specifically stated otherwise, refer to non-empty set(s) or non-empty subset(s).

Figure 1:
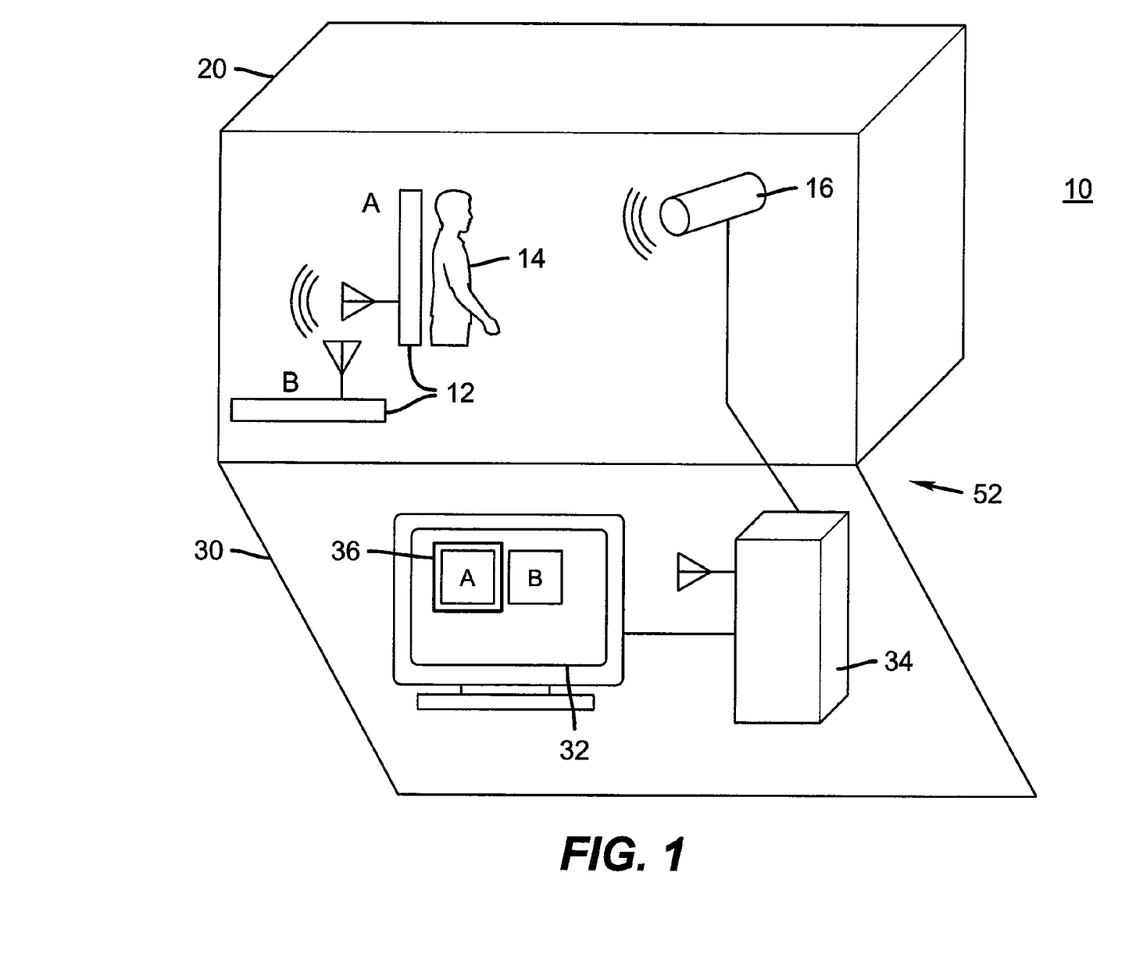
FIG. 1 is a block diagram showing an x-ray imaging room having two portable DR receiver panels.

It is instructive to consider first how this problem is addressed in embodiments of the present invention for a single DR imaging room, and then to see how this solution extends to a department in a hospital or other health care facility that has multiple imaging rooms. Referring to FIG. 1, there is shown an x-ray imaging room 10 that has an X-ray apparatus 52 that uses two wireless DR receiver panels 12, one labeled A, the other labeled B. Each DR receiver panel 12 has a unique identifying serial number or other encoding, typically assigned at time of manufacture. The wireless transmission protocol utilizes this unique encoding as a "signature" for distinguishing between any two or more DR receiver panels 12 from the same manufacturer and for setting up the proper communication channel between the panel and a controller 34.

Still referring to FIG. 1, X-ray imaging room 10 has an imaging room 20, a shielded area in which a patient 14 is imaged and containing an x-ray source 16, and a control room 30 that includes a display 32 and controller 34 for communicating with DR receiver panels 12 over a wireless interface and containing control logic for executing this function with a selected DR receiver panel 12. In the embodiment shown in FIG. 1, the image is obtained on the active DR receiver panel 12 labeled A; the DR receiver panel labeled B is inactive, not currently being used. An operator interface 36 accepts an operator instruction to select and to communicate with the active DR receiver panel 12 labeled A. In the embodiment shown, display 32 is a touchscreen display, enabling the operator or technologist to easily select either the A or the B DR receiver panel 12 as the active DR receiver panel for obtaining the image using a graphical user interface (GUI), as described in more detail subsequently.

It can be appreciated that there is some chance for operator error in the single-room environment of FIG. 1, such as mistakenly addressing and communicating with the inactive DR receiver panel 12 labeled B instead of with the active DR receiver panel 12 that is labeled A. The likelihood of error can be reduced when the operator performs a systematic procedure to position, select, and enable the DR receiver panel that is designated as "active", receiver panel A in this case, that is placed behind patient 14. Careful identification of the encoding on the DR receiver panel that is currently active can help to prevent addressing and communicating with the wrong, that is, with the "inactive" panel. However, even with carefully followed procedure, wherever there are multiple DR receiver panels 12 at a room, some opportunity for error remains.

Figure 2:
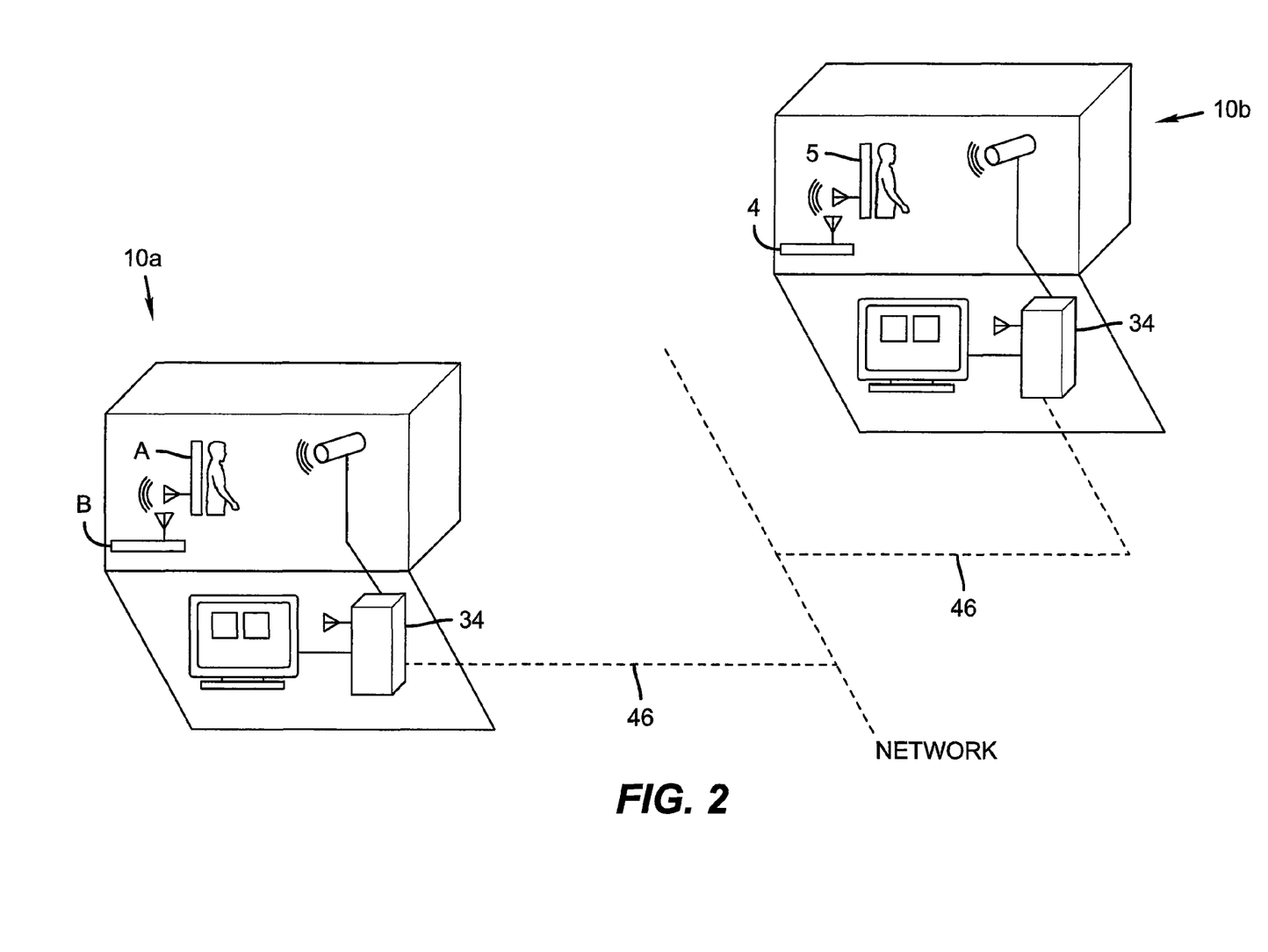
FIG. 2 is a block diagram showing a portion of a hospital or other facility having multiple x-ray imaging rooms that use DR receiver panels.

The likelihood of error for mistakenly using an inactive DR receiver panel is compounded, moreover, where a hospital or other diagnostic facility has multiple x-ray imaging rooms, as shown in the block diagram of FIG. 2. Here, a facility or department has two x-ray imaging rooms 10a and 10b. Imaging room 10a has two designated DR receiver panels 12, labeled A and B. Imaging room 10b has two designated DR receiver panels, labeled 4 and 5. As long as these DR receiver panels 12 remain at their respective rooms 10a or 10b, the likelihood of confusion and error at each room is no more difficult than that described for a single room with reference to FIG. 1. However, in the hospital environment, a crisis situation, a scheduling difficulty, or an equipment maintenance need can occur, requiring one room to borrow a DR receiver panel 12 that was originally designated for another room. For example, a low battery condition may require that one or both of the DR receiver panels 12 at x-ray imaging room 10b be temporarily out of commission. A technologist may then remove one of the DR receiver panels 12 from x-ray imaging room 10a in order to handle such a temporary emergency. In such an event, some administrative confusion is likely, resulting in the inadvertent exposure of a DR receiver panel 12 that is not properly registered with and not in active communication with the controller 34 at that room. This could mean, for example, that a technologist mistakenly exposes a patient to radiation without the proper setup and assignment of the active DR receiver panel 12. No image would be obtained from the inactive DR receiver panel that had been positioned behind the patient and a re-take and re-exposure would then be needed using the active DR receiver panel.

Figure 3:
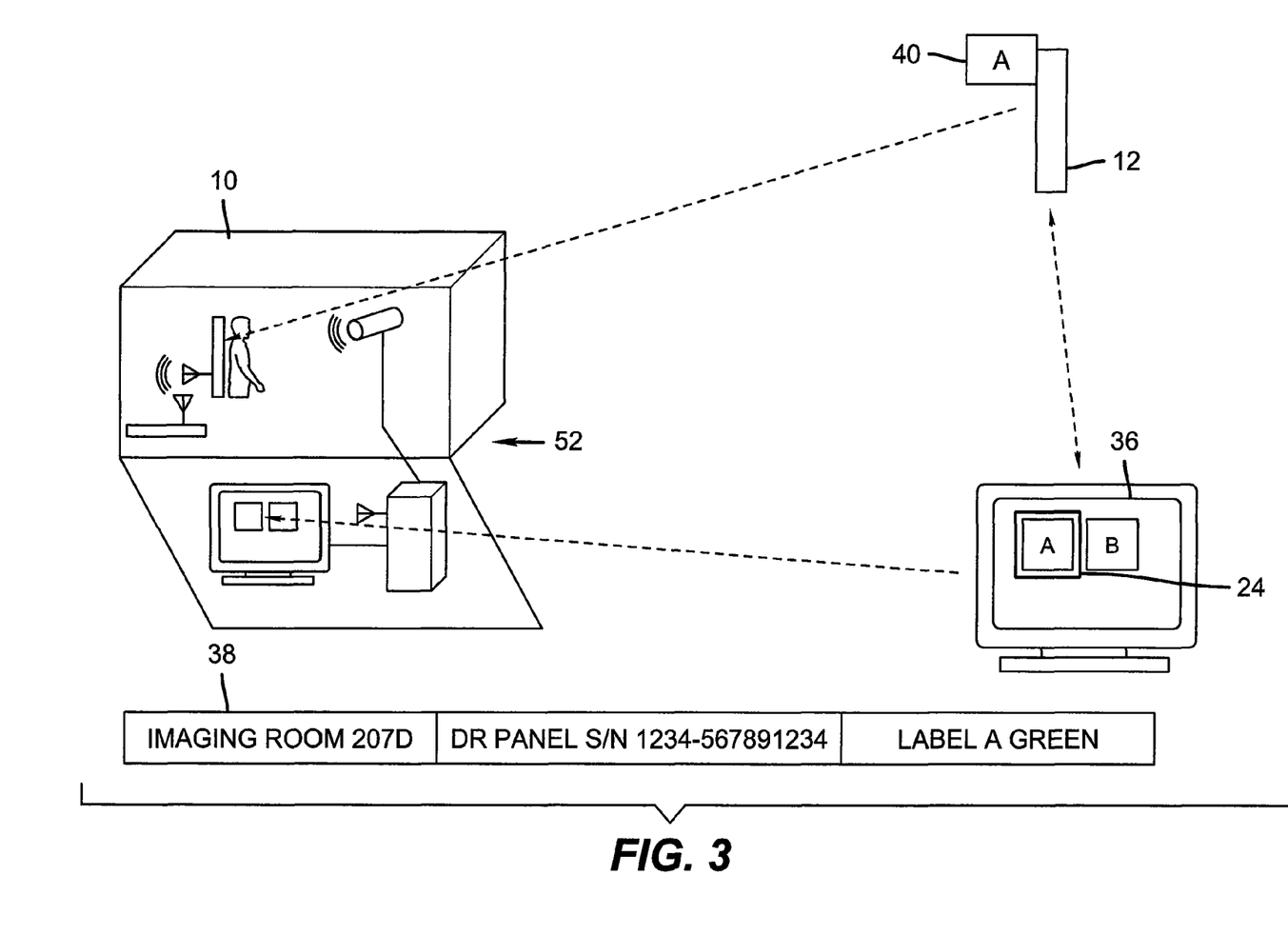
FIG. 3 shows the correlation provided between a DR receiver panel and its label, an on-screen icon, and an x-ray imaging room.

To address this problem, the apparatus and method of the present invention provide the operator with a set of visual cues and procedures for registering a DR receiver panel 12 so that it can be addressed and used within an imaging room 10 and for selecting that specific DR receiver panel 12 as the active DR receiver panel 12. As shown in FIG. 3, the registration procedure forms a unique association 38 of three specific components:

(i) a specific DR receiver panel 12;
(ii) a label that is applied to one or more surfaces of the DR receiver panel; and
(iii) an imaging room 10 that has an X-ray apparatus 52 for providing exposure energy.

By way of illustration, FIG. 3 represents association 38 as a stored data association or data structure that includes these components. The process that then selects a particular DR receiver panel 12 to make it active uses an identifying system entry, selectable by the operator or technologist, such as an on-screen icon 24. More detailed procedures for registration and selection of the active DR receiver panel are given subsequently.

Labels

Figure 4:
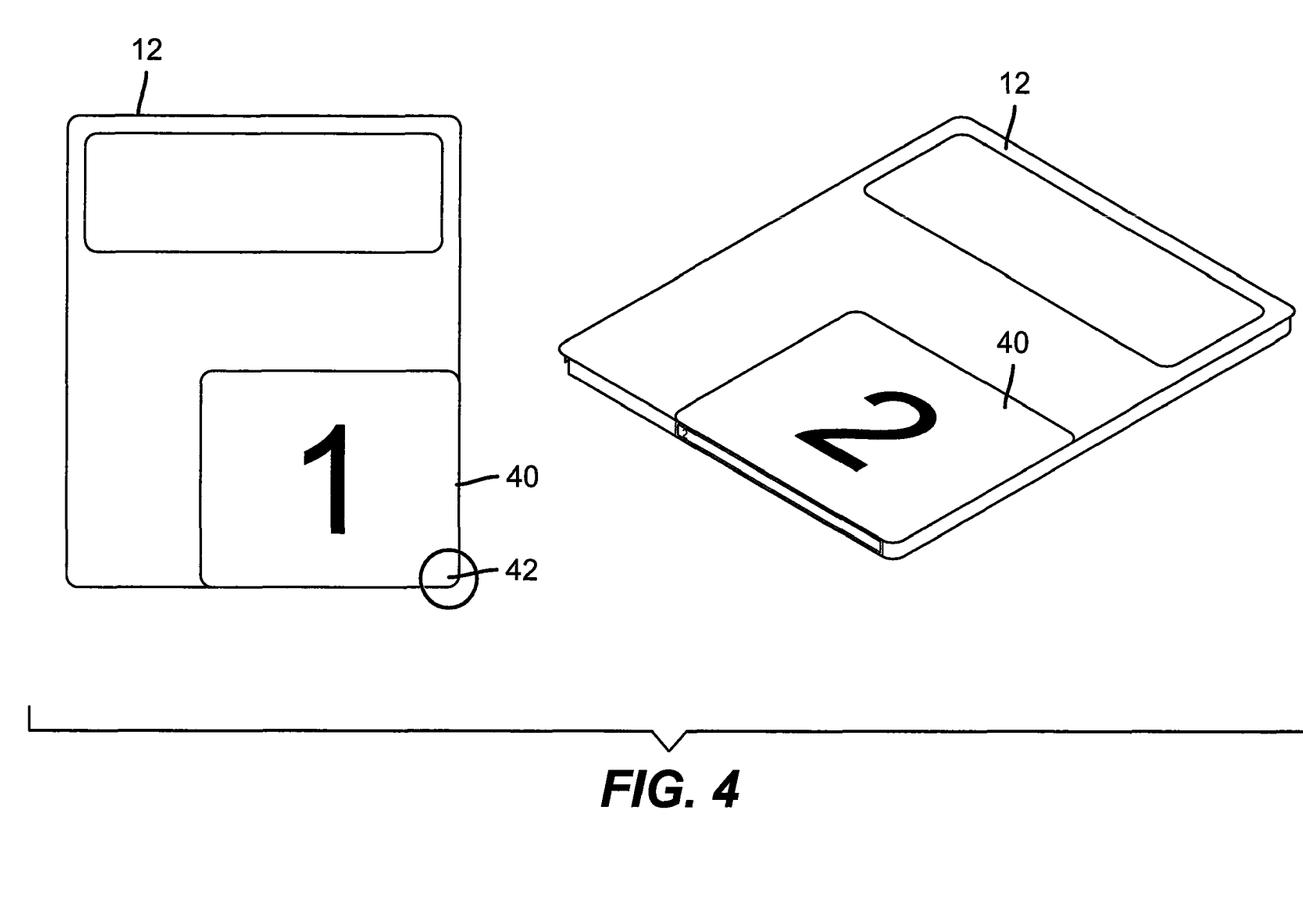
FIG. 4 shows plan and perspective views of a digital radiography receiver having a label according to one embodiment of the present invention.

The system of the present invention employs a set of labels 40, each of which can be attached or otherwise coupled to the DR receiver panel for quick visual identification of a visible marking by the operator. As shown in the example label of FIG. 4, affixed to the front face of DR receiver panel 12, a label 40 has at least two identifying coding elements that help to allow easy identification in one embodiment:

(i) a background pattern such as a color background or other pattern. The background color or pattern of the label associates the label with a room or, optionally, with a department. For example, in a hospital, a blue label may correspond to a thoracic imaging room or department, a yellow label may correspond to a room or department for pediatric imaging.

(ii) an alphanumeric character. An alphanumeric character is provided in another color that contrasts with the background color. The alphanumeric character identifies the specific DR receiver panel at the room as unique and distinguishes one DR receiver panel from another that is used in the same room.

At a minimum, at least one label marking is provided on label 40, although the use of both a background pattern such as a color (i) and an alphanumeric character (ii) further helps to avoid confusion and helps to speed identification. As shown in FIG. 4, the applied label 40 may have additional markings, such as an orientation marker 42 that helps to correctly orient the DR receiver panel within a conventional bucky, stand, or other holder. As shown in the perspective view at the right in FIG. 4, label 40, as applied, may overlap one or more edges of the DR receiver panel, or a separate edge label may be provided for improved visibility to the operator.

Figure 5:
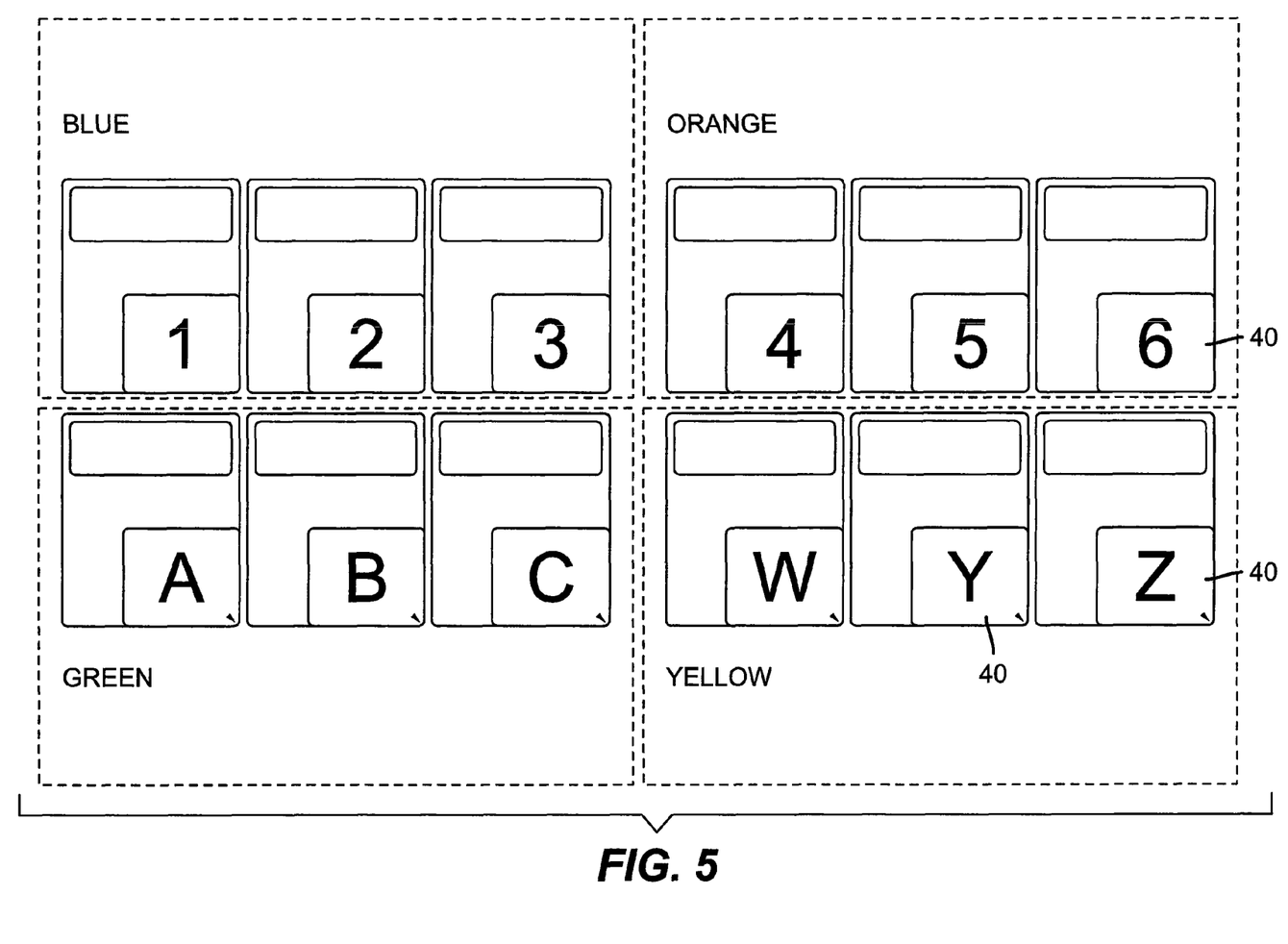
FIG. 5 shows different sets of labels to be used in a hospital or other facility having multiple x-ray imaging rooms.

In a facility that has multiple imaging rooms or departments, different background pattern or color labels 40 can be used for different imaging rooms or departments. As shown in FIG. 5, the background color, because it is unambiguous, readily identifies the DR panel as belonging to one room or department or another.

Labels 40 thus provide an intuitive identification method that allows the operator to quickly distinguish one DR receiver panel from another as to its assigned room or department and, within any particular room, referring merely to an alphanumeric character or characters appearing thereon. If a DR receiver panel is borrowed from another room or department, the operator can readily see this and then take the extra steps necessary to make sure that the DR receiver panel is properly identified and assigned as the active panel before imaging, using a registration process.

Label Materials and Configuration

Labels 40 can be from any of a number of types of substrates and can have a number of alternate arrangements, sizes, and other features, all within the scope of the present invention. Each label 40 can be applied or otherwise coupled to its DR receiver panel by being adhesively attached or may be applied or coupled by being affixed using static cling or other attractive force. Various types of fasteners could be used, as well as clear plastic pockets or brackets of some type, for example. Labels 40 can be made so that they are difficult to remove or, alternately, made to be applied with the intention of easy removal. In general, label 40 should be transparent to x-ray radiation, so that no portion of the image obtained from the patient is obscured when label 40 is used. Numbers and letters on the label may be positioned for enhanced visibility, such as by displaying numbers so that they can be easily read from either side or with the DR receiver panel upside-down, for example.

In an alternate embodiment, the DR detector panel itself includes a slotted opening or other mechanism that accepts a label or provides a window for label placement, providing coupling of the label to the DR receiver panel without requiring adhesive attachment.

Registration of the DR Receiver Panel

As noted in the description given earlier, an image can be obtained only from the DR receiver panel 12 that is both registered and active, as specified by the operator. The X-ray apparatus in each room 10 has a set of one or more registered DR receiver panels 12 from which the active DR panel is selected by the operator or technologist. As described earlier, a registration process is used to make a particular labeled DR receiver panel a member of this set. In one embodiment, steps of the registration procedure, executed using user interface 36 (FIG. 6), are as follows:

1) Read the unique encoding on the DR receiver panel. Each DR panel is manufactured or sold with a unique serial number or other encoding that is intended to distinguish it from any other DR panel that has been manufactured. Typically, this unique encoding is in the form of a bar code or similar machine-readable encoding. In one embodiment, as shown in FIG. 6, this step simply requires the operator to scan an encoded area on the DR receiver panel past a built-in bar-code scanner 26 that is part of the imaging system within a particular room.

2) Associate the unique encoding on the DR receiver panel with a specific label 40. To do this step, the operator uses operator interface 36 to match the label that is applied or otherwise coupled to the panel, with its counterpart label marking that is displayed as an icon on the operator interface.

Figure 6:
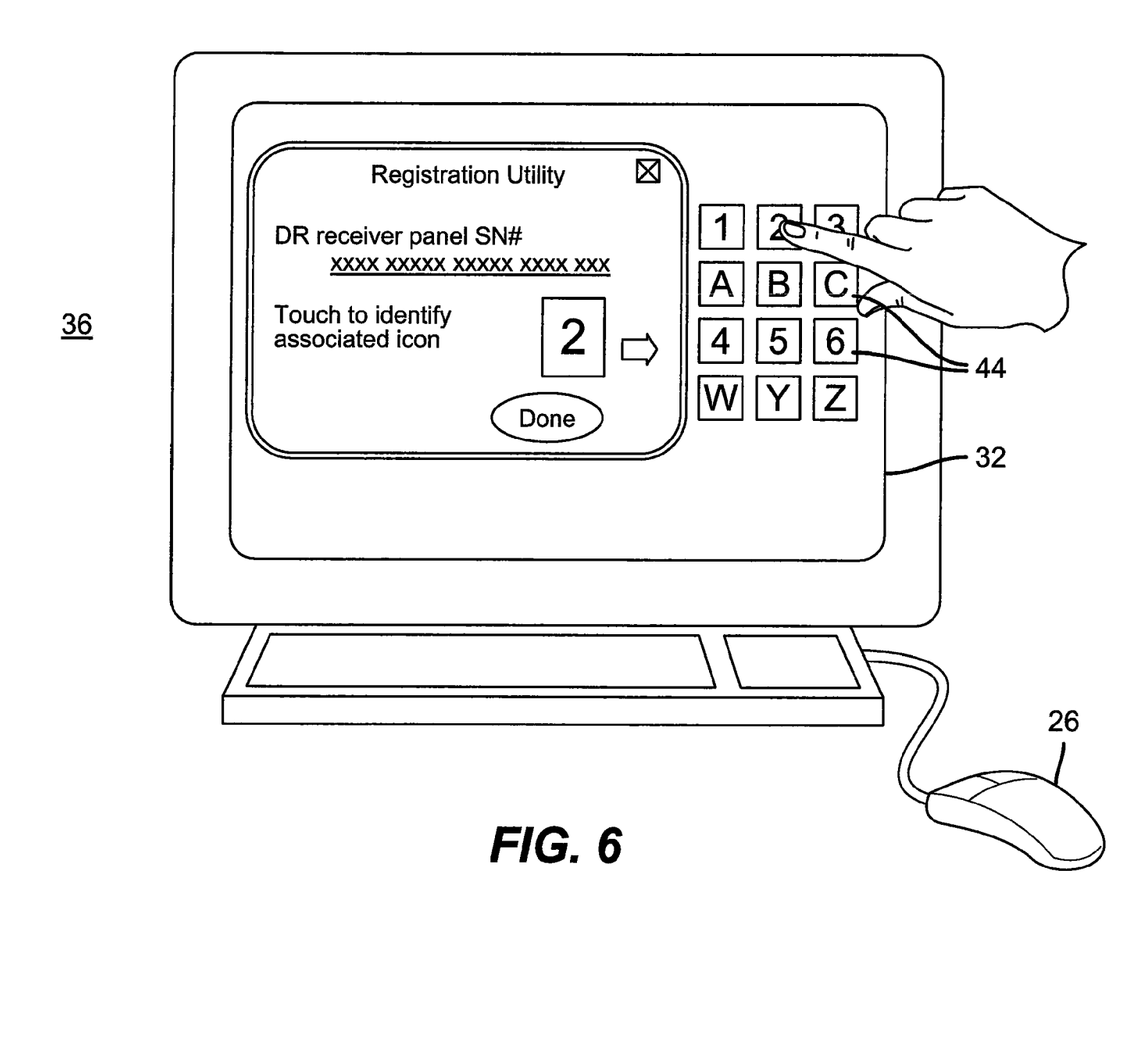
FIG. 6 shows an operator interface screen with a registration utility for DR receiver panel registration to the system.

In the example registration utility shown in FIG. 6, the operator uses a touchscreen interface to select an icon 44 from a set of available icons that match the labels available for DR receiver panels. Alternately, a mouse or other screen pointer or some other type of command entry could be used. Application software that executes the registration process includes a "library" of available label markings or designs, visually corresponding to adhesive stickers or other elements that provide the labels themselves.

The administrative task of DR receiver panel registration can be performed in any of a number of ways. Registration is performed at initial installation of the DR imaging system, but can be executed by an administrative operator or technologist whenever an unregistered DR receiver panel must be made available to the imaging apparatus within any particular room. Referring back to FIG. 2, by way of example, room 10a has two DR receiver panels, designated A and B. Green labels are used for the two DR receiver panels at room 10a. The two DR receiver panels at room 10b are designated 4 and 5 and have orange labels. An operator at room 10a may want to borrow the DR receiver panel designated 5 from room 10b, but must first use the registration procedure described with reference to FIG. 6 in order to properly address the device and access image data at room 10a.

Referring back to x-ray imaging room 10 of FIG. 1, registration provides an association that is used by controller 34 to communicate electronically with the particular DR receiver panel 12 that is active. In one embodiment, the encoded information that uniquely identifies each DR receiver panel 12 is used, in turn, to establish the wireless communication channel with the proper frequency and signal synchronization and to properly encode the wirelessly transmitted data.

Once a DR receiver panel is registered for a particular room, it is generally advantageous to retain information about that particular DR receiver panel at that room in order to permit future re-assignment of that DR receiver panel to that room.

Specifying the Active DR Receiver Panel

Figure 7:
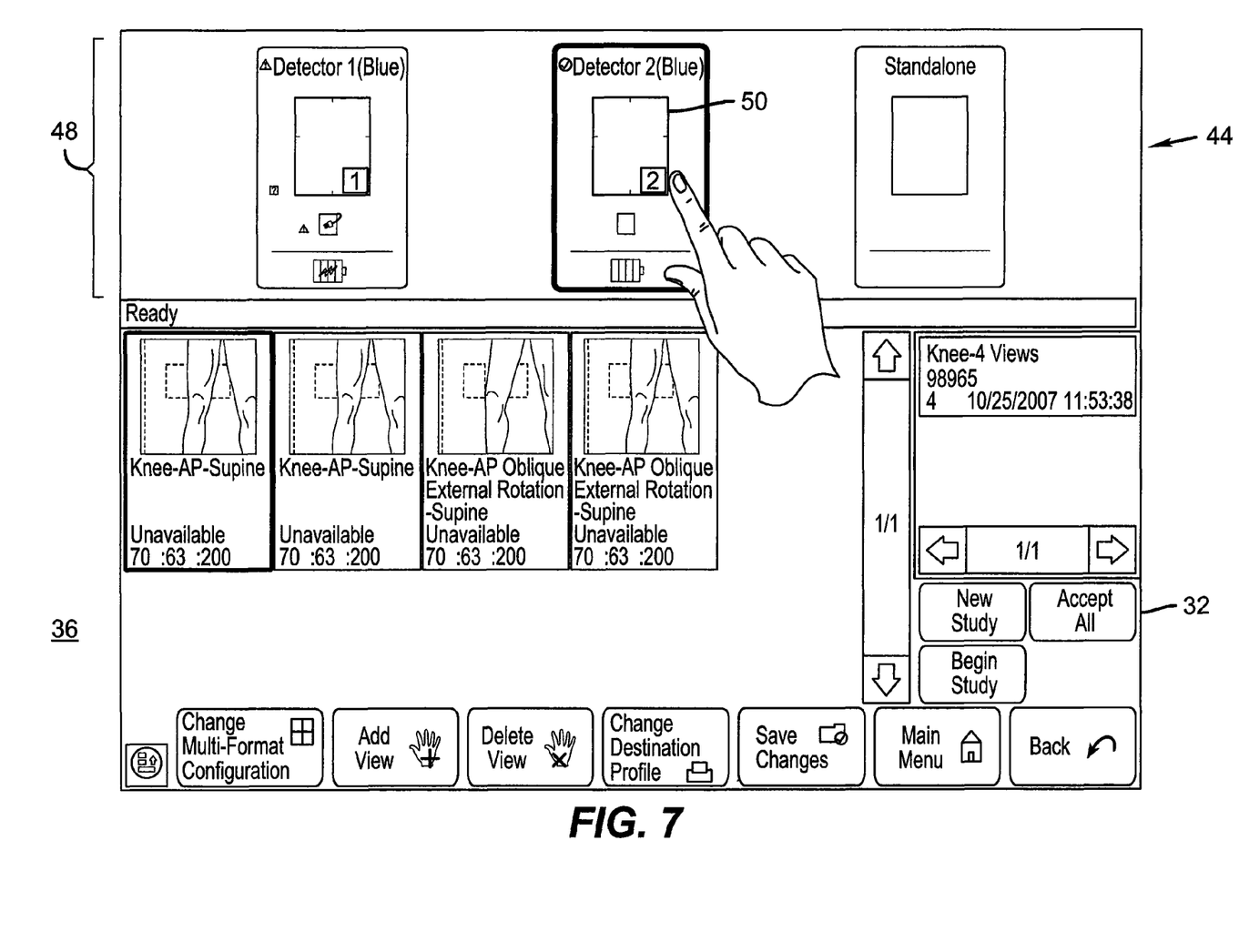
FIG. 7 shows an example of an operator interface panel for specifying one of a number of possible DR receiver panels as the active panel for imaging.

One of the registered DR receiver panels 12 in a room 10 can be active at any one time. In one embodiment, an operator entry on a user interface screen is used to assign or designate the particular active DR receiver panel. Among its many possible functions, operator interface 36 provides a mechanism for operator selection of a particular DR receiver panel as the active receiver panel in each imaging event. The example operator interface screen shown in FIG. 7 has, among its functions, a selector panel 48 that provides a selection utility for designating, as the active panel, one of the DR receiver panels that is registered to the system. By designating one member from the set of icons 44 for all DR receiver panels that are registered to the system, the operator thus sets up the communication channel for subsequent reset and exposure operations using that DR receiver panel. For positive identification, the selected icon 44 representing the active DR receiver panel is highlighted and includes a thumbnail image 50 that includes the label marking, in the embodiment shown.

Operator steps for obtaining an image of the patient can be summarized as follows:

1) Position a previously registered DR panel behind the patient in a suitable position, noting the label color and alphanumeric designation.

2) Using the operator interface, specify the DR receiver panel having that label marking as the active DR receiver panel.

3) Enter the instruction sequence to initialize the active DR receiver panel circuitry and obtain the image. In one embodiment, an initial reset instruction, transmitted wirelessly, causes the DR receiver panel to initialize and to ready its sensing circuitry for obtaining exposure energy.

4) Follow established procedures to obtain an exposure of the patient and obtain image data from the DR receiver panel.

Figure 8:
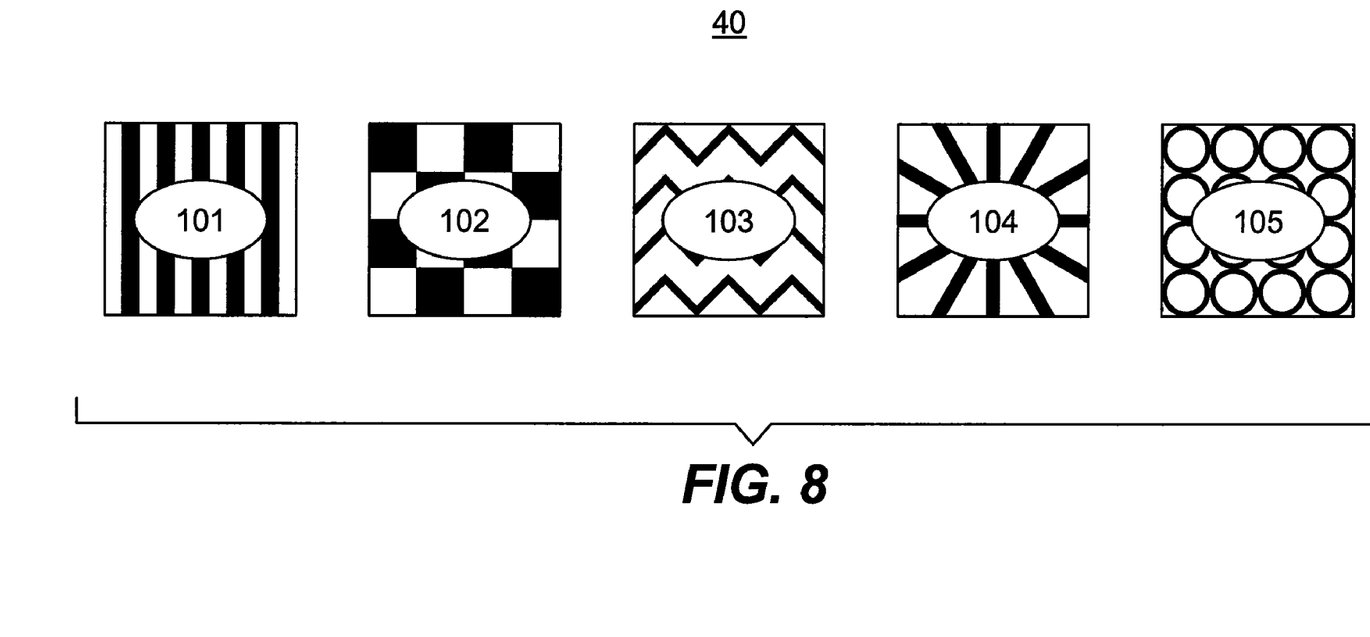
FIG. 8 shows an alternative set of labels used for a DR receiver panel that is not assigned to any one specific x-ray imaging room.

Embodiments of the present invention can take advantage of the many types of labels that can be generated. In one embodiment, a lead administrator can further designate one or more DR receiver panels as "floating" or unassigned in a system having multiple DR receiver panels. This function can be obtained by assigning a label having a black-and-white or other high-contrast pattern, rather than a color, to the DR receiver panel, then registering the panel to the imaging system at each of a number of rooms. FIG. 8 shows a set of labels 40 that can be used to designate DR receiver panels that are to be used as "floating" devices.

For the registration utility described herein, each imaging room 10 maintains its own separate library for storing the associations of registered DR receiver panels 12 with their corresponding labels 40. It can be appreciated that some form of networked communication can also be provided so that individual controllers 34 (FIG. 1) in different rooms 10 can communicate with each other and share a single library of stored association data for registered DR receiver panels 12. FIG. 2 shows, in dashed lines, an optional network connection 46 that may be provided for controller 34 at one or more imaging rooms 10. This alternate arrangement would allow registration of a DR receiver panel at a central workstation (not shown), such as at a single location that serves a hospital or other site or facility, for example, and storage of the registration information at a network-accessible memory (not shown), even where the DR receiver panel 12 is then designated for use solely within a particular room 10 or department. A data association is thus formed and stored that associates each DR receiver panel 12 at a site with its applied label 40. Then, either a central administrator or the operator or technologist at the individual room 10 enters the instruction(s) that assign or designate a particular registered DR receiver panel as the active DR receiver panel for the X-ray imaging apparatus in that room. At the individual room 10, instructions and data are then transmitted to the DR receiver panel that has been designated as active.

While there may be administrative advantages to a centralized registration scheme, there can be increased risk of operator error with centralized registration of this type, since it is done remotely with respect to the operator. Operator care is still required to make sure that the correct, registered DR receiver panel 12 is designated as active before the x-ray exposure takes place.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LIST 4,5. DR receiver panel
10, 10a, 10b. X-ray imaging room
12. DR receiver panel
14. Patient
16. X-ray source
20. Imaging room
24. Icon
26. Scanner
30. Control room
32. Display
34. Controller
36. Operator interface
38. Association
40. Label
42. Orientation marker
44. Icon
46. Network connection
48. Selector panel
50. Thumbnail image
52. X-ray apparatus
A,B. DR receiver panel

What is claimed is:

1. A method for obtaining an x-ray image comprising:
associating a control processor with one of a plurality of x-ray imaging rooms;
storing an association between a digital radiology receiver panel, a label that is applied to one or more surfaces of the digital radiology receiver panel, and an x-ray imaging room;
responding to an operator instruction by designating the digital radiology receiver panel identified by the stored association as an active digital radiology receiver panel in the x-ray imaging room;
transmitting wireless instructions to the active digital radiology receiver panel; and
obtaining image data from the active digital radiology receiver panel following exposure to x-ray radiation.

2. The method of claim 1 wherein storing the association comprises entering identifying information for the digital radiology receiver panel at the control processor that is associated with the x-ray imaging room, wherein the control processor is part of the digital radiology receiver panel, part of an x-ray imaging system or part to the x-ray imaging room.

3. The method of claim 2 wherein entering identifying information for the digital radiology receiver panel comprises scanning an encoding on the digital radiology receiver panel.

4. The method of claim 1 wherein responding to the operator instruction further comprises highlighting a display screen element that represents the designated digital radiology receiver panel.

5. The method of claim 1 wherein storing the association comprises storing data on a memory that is accessible over a network.

6. A system for obtaining an x-ray image comprising:
a plurality of x-ray imaging rooms coupled to an imaging system network, each x-ray imaging room comprising at least one x-ray system;
a first plurality of portable digital radiography receiver panels;
a second plurality of portable digital radiography receiver panels;
a label applied against one or more surfaces of the first plurality of digital radiography receiver panels and the second plurality of digital radiography receiver panels, wherein the label is selectable as a member of a set of labels, wherein each label in the set of labels has a unique label marking;
a first operator interface comprising a display that displays at least the label marking and further comprising a first selection utility that accepts an operator instruction for designating the first plurality of labeled digital radiography receiver panels as associated with a first x-ray imaging room and for designating the second plurality of labeled digital radiography receiver panels as associated with a second x-ray imaging room;
a second operator interface comprising a display that displays at least the label marking and further comprising a second selection utility that accepts an operator instruction for designating a single one of the labeled first plurality of digital radiography receiver panels as an active digital radiography receiver panel for the first x-ray imaging room and a single one of the labeled second plurality of digital radiography receiver panels as an active digital radiography receiver panel for the second x-ray imaging room; and
a wireless communication controller for communicating instructions to the designated active digital radiography receiver panel and for obtaining image data therefrom.

7. The system of claim 6 wherein the first operator interface and the second operator interface are the same operator interface.

8. The system of claim 6 wherein the selection utility at of the first operator interface accepts a subsequent operator instruction for designating one of the first plurality of labeled digital radiography receiver panels as associated with the second x-ray imaging room.

9. The system of claim 6 wherein the label is adhesively applied against the one or more surfaces of the digital radiography receiver panel.

10. The system of claim 6 wherein the label is removably coupled against the one or more surfaces of the digital radiography receiver panel.

11. The system of claim 6 wherein at least one operator interface further comprises a registration utility that associates the applied label with a unique identifier for the digital radiography receiver panel.

12. The system of claim 6 wherein the operator interfaces use a touchscreen.

13. The system of claim 6 wherein the unique marking on the label comprises an alphanumeric character on a color background, and wherein the unique label marking separates each labeled digital radiography receiver panel into one of a plurality of subsets, each subset associated with an x-ray imaging room of a plurality of x-ray imaging rooms on the network.

14. The system of claim 13 wherein the selection utility accepts an operator instruction for designating a third plurality of labeled digital radiography receiver panels as floating and associated with more than one of the plurality of x-ray imaging rooms.

15. The system of claim 14 wherein the first and second operator interfaces are the same operator interface, or wherein the first and second operator interfaces are different interfaces and the second operator interfaces comprises a plurality of third operator interfaces where each of the third operator interfaces are each individually associated with a single one of the plurality of x-ray imaging rooms.

16. A method for obtaining an x-ray image comprising:
forming an imaging system network by connecting a plurality of separate x-ray imaging rooms, the plurality of separate x-ray imaging rooms each comprising at least one x-ray apparatus;
identifying a first plurality of portable digital radiography receiver panels;
identifying a second plurality of portable digital radiography receiver panels;
exposing a label of a set of labels against one or more surfaces of the first plurality of digital radiography receiver panels and the second plurality of digital radiography receiver panels, wherein the label is selectable as a member of the set of labels and a member of at least one of a plurality of subsets of the set of labels, wherein each label in the set of labels has a unique label marking;
forming at least first and second data associations, each data association uniquely associating a digital radiology receiver panel with a label that is applied to one or more surfaces of the digital radiology receiver panel;
designating the first data associations as identifying an active digital radiology receiver panel for a particular X-ray imaging room;
designating the second data associations as establishing a correspondence between a first subset of the labels, the first plurality of portable digital radiography receiver panels and a first x-ray imaging room, establishing the correspondence between a second subset of the labels, the second plurality of portable digital radiography receiver panels and a second x-ray imaging room, and establishing the correspondence between a third subset of the labels and more than one x-ray imaging rooms;
transmitting wireless instructions to the active digital radiology receiver panel; and
obtaining image data from the active digital radiology receiver panel following exposure to x-ray radiation.

17. The method of claim 16 further comprising storing the at least first and second data associations in a network-accessible memory, wherein the third subset of labels identify floating digital radiography receiver panels, comprising changing one of the second data associations to modify the correspondence of one of the first digital radiography receiver panel to the second x-ray imaging room.

* * * * *